United States Patent
Jeon

(10) Patent No.: US 9,814,472 B2
(45) Date of Patent: Nov. 14, 2017

(54) SURGICAL INSTRUMENT FOR REMOVING HOOK NOSE BONE

(71) Applicant: Seong Ha Jeon, Seoul (KR)

(72) Inventor: Seong Ha Jeon, Seoul (KR)

( * ) Notice: Subject to any disclaimer, the term of this patent is extended or adjusted under 35 U.S.C. 154(b) by 380 days.

(21) Appl. No.: 14/438,542

(22) PCT Filed: Sep. 6, 2013

(86) PCT No.: PCT/KR2013/008085
§ 371 (c)(1),
(2) Date: Apr. 24, 2015

(87) PCT Pub. No.: WO2014/065506
PCT Pub. Date: May 1, 2014

(65) Prior Publication Data
US 2015/0265289 A1    Sep. 24, 2015

(30) Foreign Application Priority Data
Oct. 26, 2012  (KR) ........................ 10-2012-0119399

(51) Int. Cl.
*A61B 17/16* (2006.01)
*A61B 17/17* (2006.01)

(52) U.S. Cl.
CPC ...... *A61B 17/1688* (2013.01); *A61B 17/1604* (2013.01); *A61B 17/1785* (2016.11)

(58) Field of Classification Search
CPC ............ A61B 17/1688; A61B 17/1604; A61B 17/1785
See application file for complete search history.

(56) References Cited

U.S. PATENT DOCUMENTS 3,667,470 A * 6/1972 Rubin ............... A61B 17/1604
30/356
3,716,057 A * 2/1973 Rubin ............... A61B 17/1604
30/168
(Continued)

FOREIGN PATENT DOCUMENTS

GR    WO 9113536 A2 * 9/1991 ......... A61B 17/1604
JP    2007-159939 A    6/2007
(Continued)

OTHER PUBLICATIONS

PCT/KR2013/008085 International Search Report dated Dec. 3, 2013; 3pgs.

*Primary Examiner* — Christian Sevilla
(74) *Attorney, Agent, or Firm* — Bracewell LLP; Brad Y. Chin

(57) ABSTRACT

Embodiments of the invention provide a surgical instrument for removing a hook nasal hump. The surgical instrument includes a handle including a blade having a prominent edge at a front end thereof, and guide members coupled to both sides of the handle and configured to slide the handle; forward and backward. The surgical instrument further includes a mounting concave portion configured to mount the nasal hump, which is a surgical subject, formed at a front portion of the guide members, and an upper and a lower plate, each having a shape of a flat sheet and a predetermined length. The blade of the handle is integrated between the upper plate and the lower plate, a width of the blade is smaller than a width of the upper and lower plates, sliding grooves are formed between both sides of the blade and the upper and lower plates, and the guide members comprise rod-shaped rails inserted into the sliding grooves, so as to slide the handle. The surgical instrument further includes mounting rods of which one side of each mounting rod is (Continued)

coupled to a front portion of each rail and of which the other side is coupled to the mounting concave portion for hooking onto the nasal hump.

3 Claims, 3 Drawing Sheets

(56) References Cited

U.S. PATENT DOCUMENTS

| | | | |
|---|---|---|---|
| 4,697,586 A * | 10/1987 | Gazale | A61B 17/1604 606/53 |
| 6,595,996 B2 | 7/2003 | Dinger et al. | |
| 2001/0005786 A1 | 6/2001 | Michelson | |

FOREIGN PATENT DOCUMENTS

| | | |
|---|---|---|
| JP | 2011-130796 A | 7/2011 |
| JP | 2003-339723 A | 12/2013 |
| KR | 10-1987-0002816 A | 4/1987 |

* cited by examiner

SURGICAL INSTRUMENT FOR REMOVING HOOK NOSE BONE

CROSS REFERENCE TO RELATED APPLICATION

This application claims the benefit of and priority to PCT/KR2013/008085 filed on Sep. 6, 2013, entitled (translation), "SURGICAL INSTRUMENT FOR REMOVING HOOK NOSE BONE," which claims the benefit of and priority to Korean Patent Application No. KR 10-2012-0119399 filed on Oct. 26, 2012, entitled (translation), "SURGICAL INSTRUMENT FOR NASAL HUMP REMOVAL," both of which are hereby incorporated by reference in their entirety into this application.

BACKGROUND

Field of the Invention

Embodiments of the invention relate to a surgical instrument which is used to operate a book nose, and more particularly to a surgical instrument for removing a hook nose hump through an osteotomy of the nasal hump of the hook nose having the prominent nasal hump.

Description of the Related Art

A nose having a prominent nasal hump from the ridge of the nose is called a hook nose. The hook nose is not beautiful aesthetically and causes a bad impression. Therefore, it is very important to remove the hook nose hump in rhinoplasty. The hook nose hump is removed by being cut or ground. Cutting the bone is called an osteotomy and a surgical instrument which is used in osteotomy is called an osteotome.

An existing surgical instrument for cutting the hook nose hump includes an osteotome, as described, for example, in U.S. Pat. No. 3,716,057. The osteotome includes a stabilizer in which an arch-shaped concave portion is formed on the handle and includes an integral blade which has an edge and protrusion formed on one side of the handle. This intends to remove the hook nose hump through an osteotomy of the hook nose hump by means of the blade by holding the stabilizer of the osteotome in operation. In the osteotomy, it is difficult to properly maintain the angle and height of the osteotome. As a result, there is a risk of removing too much or too little hook nose hump.

SUMMARY

Embodiments of invention maintain the operation angle and height of the surgical instrument in an osteotomy and removal of the prominent nasal hump of a hook nose.

Embodiments of the invention tallow a user to easily hold the nasal hump surgical instrument and to make it easier to perform the osteotomy of the nasal hump by means of a blade sliding from a guide member.

According to an embodiment, there is provided a surgical instrument for removing a hook nose hump. According to at least one embodiment, guide members for forward and backward sliding a handle are coupled to the both sides of the handle including a blade having a prominent edge at the front end thereof. A mounting concave portion for mounting the nasal hump, which is a surgical subject, is formed at the front portion of the guide members.

According to an embodiment, the blade of the handle is integrated between an upper plate and a lower plate having the shape of a flat sheet and having a predetermined length. The width of the blade is smaller than the width of the upper and lower plates. Sliding grooves are respectively formed between the both sides of the blade and the upper and lower plates. The guide members include rod-shaped rails respectively inserted into the sliding grooves so as to slide the handle, and mounting rods of which one side is coupled to the front portions of the rails and of which the other side has mounting concave portions capable of being hooked onto the nasal hump.

According to an embodiment, a stopper, which limits the sliding of the lower plate, is formed at one of the rails to which one of the mounting rods is coupled. According to an embodiment, the surgical instrument includes a stopper formed at each rail.

According to an embodiment, the surgical instrument further includes an interval maintaining portion which is coupled to a side end or lower portion of the rails and makes it possible for the rails to maintain a constant interval.

According to an embodiment, the surgical instrument further includes a stabilizer which protrudes from and is coupled to the top of the upper plate of the handle and moves forward and backward the handle.

According to an embodiment, a concave portion is formed on right and left sides of the stabilizer.

According to an embodiment, a riser portion is formed on both sides of the edge.

According to at least one embodiment, the surgical instrument facilitates the osteotomy of the nasal hump since the handle coupled to the guide members can be forward and backward slid, provides convenience of surgical operation through the selection of the osteotomy angle of the nasal hump and the maintenance of proper angle and height of the surgical instrument since the mounting concave portions formed at the mounting rods of the guide members can be hooked onto the nasal hump, reduces the surgical time for the osteotomy of the nasal hump, and enables more precise and stable surgical operation.

Various objects, advantages and features of the invention will become apparent from the following description of embodiments with reference to the accompanying drawings.

BRIEF DESCRIPTION OF DRAWINGS

These and other features, aspects, and advantages of the invention are better understood with regard to the following Detailed Description, appended Claims, and accompanying Figures. It is to be noted, however, that the Figures illustrate only various embodiments of the invention and are therefore not to be considered limiting of the invention's scope as it may include other effective embodiments as well.

DETAILED DESCRIPTION

Figure 1:
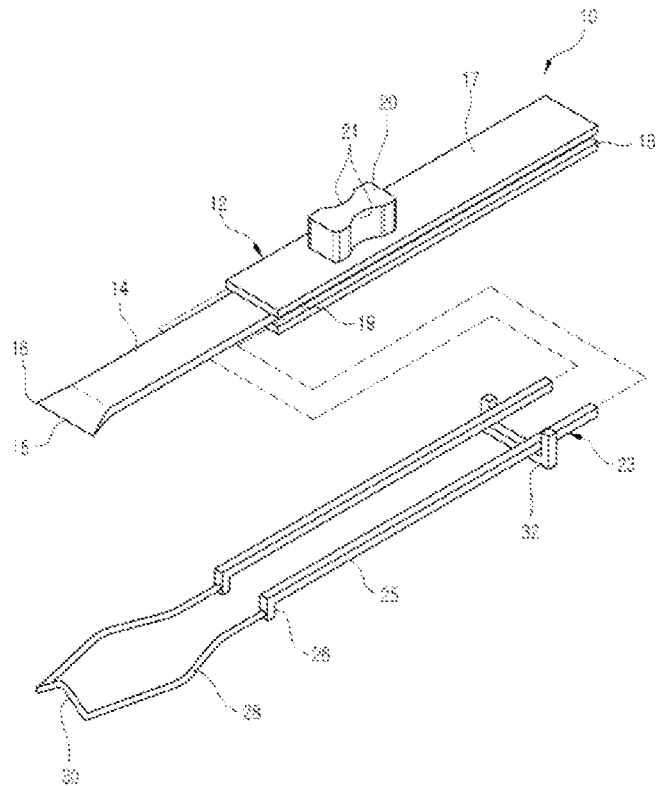
FIG. 1 is an exploded perspective view showing a surgical instrument for removing a hook nose hump according to an embodiment of the invention.

Hereafter, a surgical instrument for removing a hook nose hump according to various embodiments of the invention will be described in detail with reference to the accompanying drawings.

Advantages and features of the invention and methods of accomplishing the same will be apparent by referring to embodiments described below in detail in connection with the accompanying drawings. However, the invention is not limited to the embodiments disclosed below and may be implemented in various different forms. The embodiments are provided only for completing the disclosure of the invention and for fully representing the scope of the invention to those skilled in the art.

For simplicity and clarity of illustration, the drawing figures illustrate the general manner of construction, and descriptions and details of well-known features and techniques may be omitted to avoid unnecessarily obscuring the discussion of the described embodiments of the invention. Additionally, elements in the drawing figures are not necessarily drawn to scale. According to at least one embodiment, the dimensions of some of the elements in the figures may be exaggerated relative to other elements to help improve understanding of embodiments of the invention. Like reference numerals refer to like elements throughout the specification.

Referring to FIG. 1, a surgical instrument 10 for removing a hook nose hump, according to at least one embodiment, includes a handle 12 and guide members 23, which support the handle in a sliding manner and maintains an osteotomy angle. According to at least one embodiment, the guide members 23 for forward and backward sliding the handle 12 are coupled to the both sides of the handle 12, which includes a blade 14 having a prominent edge 15 at the front end thereof. Also, a mounting concave portion 30 for mounting a nasal hump, which is a surgical subject, is formed at the front portion of the guide members 23.

According to at least one embodiment, the surgical instrument 10 further includes an upper plate 17 and a lower plate 18 having the shape of a flat sheet and having a predetermined length. The upper plate 17 and the lower plate 18 are integrally coupled to the top and bottom of the blade 14 of the handle 12. The blade 14 is more prominent than the upper plate 17 and the lower plate 18. According to at least one embodiment, the blade 14 has a structure allowing the upper plate 17 and the lower plate 18 to be replaced with each other, but is not limited thereto.

According to at least one embodiment the width of the blade 14 is smaller than the width of the upper plate 17 and the width of the lower plate 18. As further shown in FIG. 1, sliding grooves 19 are respectively formed between the both sides of the blade 14 and the upper and lower plates 17 and 18. Also, a riser portion 16 is formed on both sides of the edge 15. According to at least one embodiment, the width the riser portion 16 of the edge 15 becomes larger than the width of the blade 14 toward the front end portion of the blade 14 from the body of the blade 14. Therefore, the width of the portion of the edge 15, which performs the osteotomy, is increased.

According to at least one embodiment, a knob-shaped stabilizer 20 protrudes from and is coupled to the top of the upper plate 17 of the handle 12. The handle 12 is moved forward and backward by pushing or pulling the stabilizer 20 with a finger, etc. Also, a concave portion 21 is formed on right and left sides, for example, of the stabilizer 20 and has a shape allowing the stabilizer 20 to be easily held by the finger. Also, protrusions or unevenness, etc., is formed on the surface of the stabilizer 20, thereby preventing the finger from being slid.

Figure 2A:
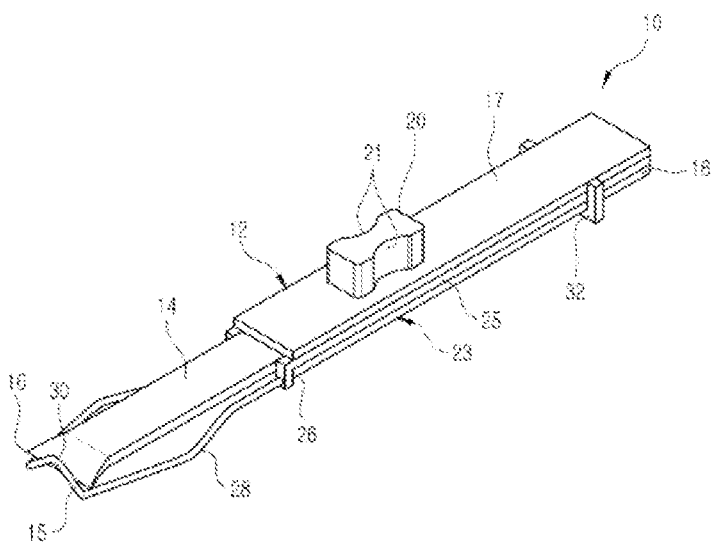
FIGS. 2a and 2b are combined perspective views showing the surgical instrument for removing the hook nose hump according to an embodiment of the invention.
Figure 2B:
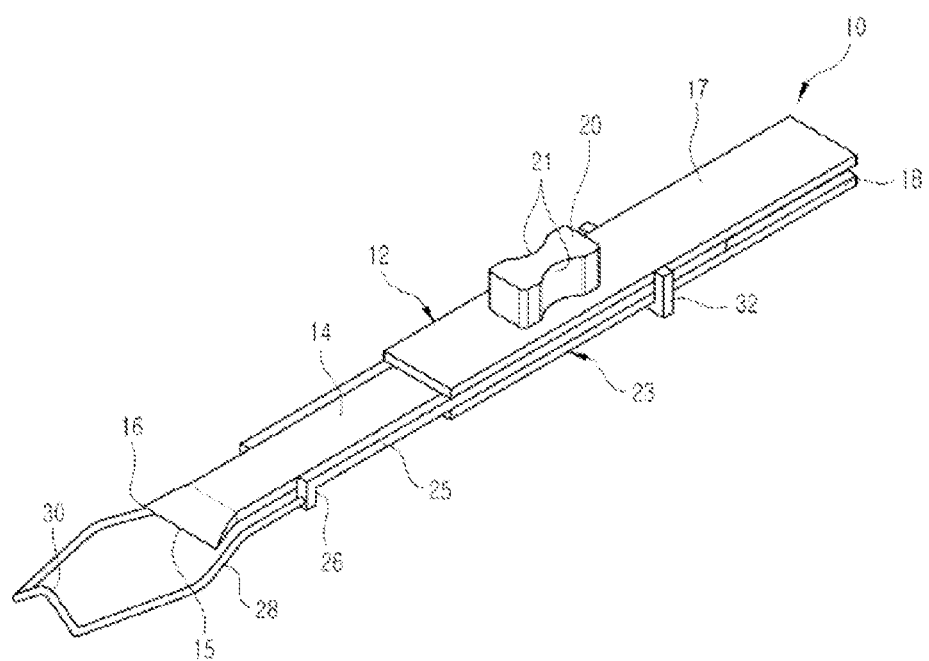

According to at least one embodiment, as shown in FIGS. 2a and 2b, the guide members 23 support the handle 12 and slide the handle 12 forward and backward. The guide-members 23 include rod-shaped rails 25, which are inserted respectively into the sliding groove 19. A mounting rod 28 is coupled to the front portion of each of the rails 25. The mounting concave portion 30 is configured to hook onto the nasal hump, which is a surgical subject, and is formed at the end portion of the mounting rod 28. It is recommended that the shape of the mounting concave portion 30 should be an approximate circular arc shape or a triangular shape to be hooked or mounted onto the nasal hump.

According to at least one embodiment, as further shown in FIGS. 2a and 2b, a stopper 26, which limits the sliding of the lower plate 18, is formed at the front portion of each rail 25, i.e., the portion to which the mounting rod 28 is coupled. The stopper 26 is formed by bending the rail 25 at an approximate right angle and limits the forward movement of the lower plate 18. It is desirable to limit in such a manner that the edge 15 of the blade 14 moves only up to the vicinity of the top or rear of the mounting concave portion 30.

According to at least one embodiment, as further shown in FIGS. 2a and 2b, an interval maintaining portion 32 is coupled to either the side ends of the rails 25 or the lower portion of the rails 25. The interval maintaining portion 32 maintains a constant interval between the rails 25, thereby firmly supporting the forward and backward sliding of the handle 12. The interval maintaining portion 32 includes a function of allowing an operator to mount his/her finger. For example, when the operator places his/her thumb at the front portion of the interval maintaining portion 32, the interval maintaining portion 32 performs a function as a fulcrum, enabling the operator to push the stabilizer 20 of the handle 12 with his/her thumb.

FIGS. 2a and 2b show that the handle 12 and the guide members 23 have been integrally combined with each other. FIG. 2a shows that the handle 12 has moved forward from the guide members 23. As a result, the edge 15 of the blade 14 comes in contact with the nasal hump, i.e., the surgical object. FIG. 2b shows that the handle 12 has moved backward along the rails 25 of the guide members 23.

Figure 3:
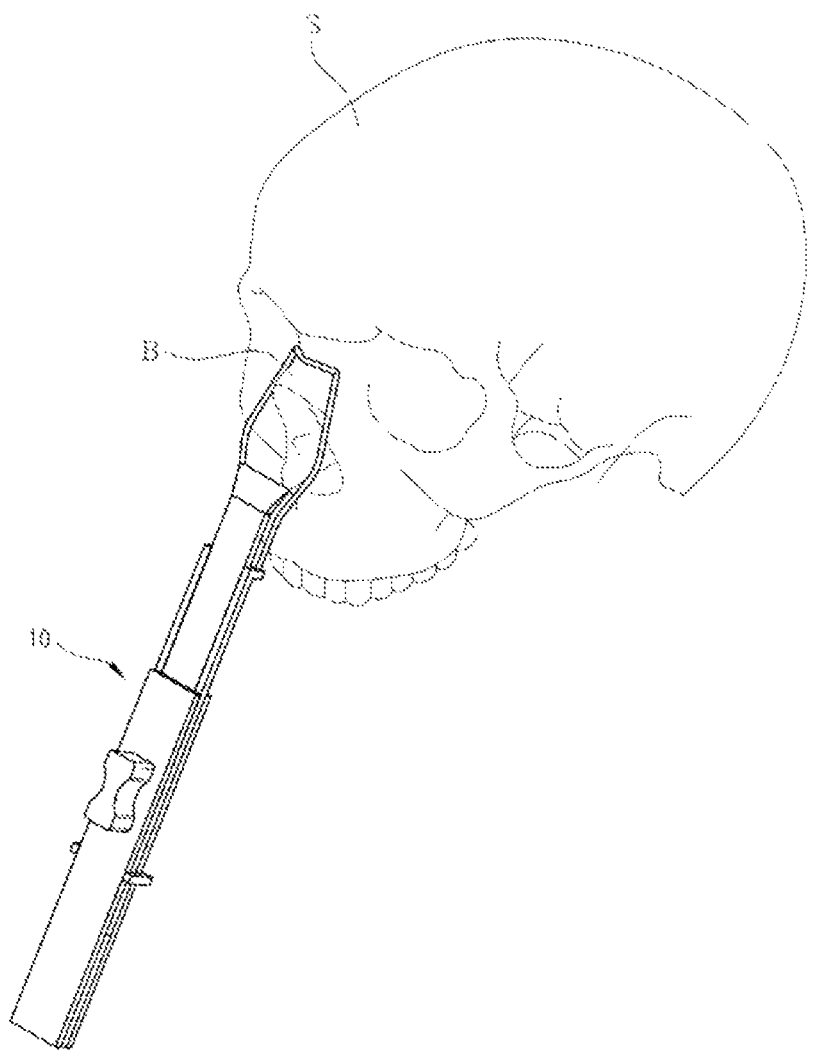
FIG. 3 shows a state where the nasal hump is removed by using the surgical instrument for removing the hook nose hump according to an embodiment of the invention.

FIG. 3 shows a state where the nasal hump of the hook nose is operated by using the surgical instrument 10 for removing the hook nose hump according to at least one embodiment of the invention. Under the state where the mounting concave portion 30 of the mounting rod 28 is mounted on the nasal hump "B" of a skull "S", the osteotomy of the nasal hump "B" is performed with the blade 14 by hitting the handle 12 with a hammer.

When the osteotomy of the nasal hump "B" is performed, the mounting concave portion 30 is positioned on the nose root portion, which is the lowest portion of the nasal hump. The mounting concave portion 30 allows the surgical instrument 10 to have a proper angle and height so as not to be inclined excessively downward or upward or allows the surgical instrument 10 to maintain a certain angle.

The surgical instrument 10 according to an embodiment of the invention makes it easier to maintain the osteotomy angle of the nasal hump "B" of the hook nose by the rails 25, which slides the handle 12 forward and backward and by the guide members 23, which include the mounting concave portion 30 of the mounting rod 28, thereby reducing the surgical time and enabling more precise surgical operation. Embodiments of the invention eliminate the danger by preventing the surgical instrument 10 from being inclined excessively downward and prevents the insufficient osteotomy by causing the surgical instrument 10 not to be inclined excessively upward.

Terms used herein are provided to explain embodiments, not limiting the invention. Throughout this specification, the singular form includes the plural form unless the context clearly indicates otherwise. When terms "comprises" and/or "comprising" used herein do not preclude existence and addition of another component, step, operation and/or device, in addition to the above-mentioned component, step, operation and/or device.

Embodiments of the invention may suitably comprise, consist or consist essentially of the elements disclosed and may be practiced in the absence of an element not disclosed. According to at least one embodiment, it can be recognized by those skilled in the art that certain steps can be combined into a single step.

The terms and words used in the specification and claims should not be interpreted as being limited to typical meanings or dictionary definitions, but should be interpreted as having meanings and concepts relevant to the technical scope of the invention based on the rule according to which an inventor can appropriately define the concept of the term to describe the best method he or she knows for carrying out the invention.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments of the invention described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated, steps may possibly be omitted and/or certain other steps not described herein may possibly be added to the method.

The singular forms "a," "an," and "the" include plural referents, unless the context clearly dictates otherwise.

As used herein and in the appended claims, the words "comprise," "has," and "include" and all grammatical variations thereof are each intended to have an open, non-limiting meaning that does not exclude additional elements or steps.

As used herein, it will be understood that unless a term such as 'directly' is not used in a connection, coupling, or disposition relationship between one component and another component, one component may be 'directly connected to', 'directly coupled to' or 'directly-disposed to' another element or be connected to, coupled to, or disposed to another element, having the other element intervening therebetween.

As used herein, the terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein. The term "coupled," as used herein, is defined as directly or indirectly connected in an electrical or non-electrical manner. Objects described herein as being "adjacent to" each other may be in physical contact with each other, in close proximity to each other, or in the same general region or area as each other, as appropriate for the context in which the phrase is used. Occurrences of the phrase "according to an embodiment" herein do not necessarily all refer to the same embodiment.

Although the invention has been described in detail, it should be understood that various changes, substitutions, and alterations can be made hereupon without departing from the principle and scope of the invention. Accordingly, the scope of the invention should be determined by the following claims and their appropriate legal equivalents.

The invention claimed is:

1. A surgical instrument for removing a hook nasal hump, the surgical instrument comprising:
   a handle comprising a blade having a prominent edge at a front end thereof;
   guide members coupled to both sides of the handle and configured to slide the handle forward and backward;
   a mounting concave portion configured to mount the nasal hump, which is a surgical subject, formed at a front portion of the guide members,
   an upper and a lower plate, each having a shape of a flat sheet and a predetermined length,
   wherein the blade of the handle is integrated between the upper plate and the lower plate,
   wherein a width of the blade is smaller than a width of the upper and lower plates,
   wherein sliding grooves are formed between both sides of the blade and the upper and lower plates, and
   wherein the guide members comprise rod-shaped rails inserted into the sliding grooves, so as to slide the handle,
   the surgical instrument further comprising:
   mounting rods of which one side is coupled to front portions of the rails and of which the other side is coupled to the mounting concave portion for hooking onto the nasal hump.

2. The surgical instrument of claim 1, further comprising:
   a stopper configured to limit the sliding of the lower plate, the stopper being formed at one of the rails to which one of the mounting rods is coupled.

3. The surgical instrument of claim 1, further comprising:
   an interval maintaining portion, which is coupled to one of a side end or a lower portion of one of the rails and is configured such that the rails maintain a constant interval.

\* \* \* \* \*